United States Patent [19]

Faryniarz et al.

[11] Patent Number: 5,723,113
[45] Date of Patent: *Mar. 3, 1998

[54] SPRAYABLE HAIR TREATMENT COMPOSITION

[75] Inventors: Joseph Raymond Faryniarz, Oxford; G. Jae Lee, Trumbull; Paul Vinski, Danbury; Frank Jones, Gilford, all of Conn.

[73] Assignee: Chesebrough-Pond's USA Co., Division of Conopco, Inc., Greenwich, Conn.

[*] Notice: The term of this patent shall not extend beyond the expiration date of Pat. No. 5,599,532.

[21] Appl. No.: 736,298

[22] Filed: Oct. 24, 1996

Related U.S. Application Data

[62] Division of Ser. No. 289,737, Aug. 12, 1994, Pat. No. 5,599,532.

[51] Int. Cl.$^6$ .................................................. A61K 00/00
[52] U.S. Cl. .................... 424/70.16; 424/47; 424/70.11; 424/DIG. 1; 424/DIG. 2; 424/78.18
[58] Field of Search ...................... 424/47, 70.11, 424/70.16, DIG. 1, DIG. 2, 78.18; 524/903; 525/318.4, 329.7, 329.9, 330.2, 330.3, 330.5; 526/317.1, 318.2

[56] References Cited

U.S. PATENT DOCUMENTS

| | | |
|---|---|---|
| 3,927,199 | 12/1975 | Micchelli et al. . |
| 4,261,972 | 4/1981 | Nandagiri et al. . |
| 4,402,977 | 9/1983 | Grollier et al. . |
| 4,543,249 | 9/1985 | Nelson . |
| 4,859,455 | 8/1989 | Nowak, Jr. et al. ............. 424/47 |
| 4,874,604 | 10/1989 | Sramek ............................ 424/47 |
| 4,983,383 | 1/1991 | Maksimoski et al. . |
| 5,021,238 | 6/1991 | Martino et al. ................... 424/47 |
| 5,068,099 | 11/1991 | Sramek . |
| 5,294,437 | 3/1994 | Shah et al. . |
| 5,304,368 | 4/1994 | Shernov et al. . |
| 5,306,484 | 4/1994 | Potthoff-Karl et al. . |
| 5,413,775 | 5/1995 | Hatfield et al. ................... 424/47 |
| 5,441,728 | 8/1995 | Tsaur et al. . |
| 5,501,851 | 3/1996 | Mudge et al. . |
| 5,576,137 | 11/1996 | Frass et al. ....................... 430/166 |
| 5,589,157 | 12/1996 | Hatfield ............................ 424/47 |

FOREIGN PATENT DOCUMENTS 0 590 604  4/1994  European Pat. Off. .

Primary Examiner—Robert H. Harrison
Attorney, Agent, or Firm—Milton L. Honig

[57] ABSTRACT

A hairspray composition is described that includes a nonionic polymer and an anionic polymer. The nonionic polymer is formed from monomers having at least one unneutralized carboxylic acid. The anionic polymer is identical to the nonionic one, except that all of the carboxylic acid groups are in salt form. Advantageously, the composition further includes an acrylic resin, most especially an amphoteric one. Best results are achieved when the acrylic resin is neutralized with a relatively small cation such as potassium and a second cation of a water soluble fatty amine. These compositions employ water as the carrier and dimethyl ether as propellant.

13 Claims, No Drawings

SPRAYABLE HAIR TREATMENT COMPOSITION

This is a Divisional application of Ser. No. 08/289,737 filed Aug. 12, 1994 now U.S. Pat. No. 5,599,532.

BACKGROUND OF THE INVENTION

1. Field of the Invention

The invention relates to hairspray compositions, especially those formulated to meet VOC emission standards.

2. The Related Art

Chemically based consumer products have come under ever increasing environmental scrutiny. Spray formulations have been particularly impacted by environmental concerns. Legislation has been enacted to ban chlorofluorocarbons as propellants in aerosol spray compositions. Successor propellants in the form of volatile hydrocarbons have also come under scrutiny. Not only propellants but even solvents such as ethanol are undergoing restriction.

California's legislation concerning volatile organic compounds (VOC) has forced future hairspray products to replace, at least in part, the organic solvent with water. Concentrations of organic propellants present in water-based solvents must also be adjusted to relatively low levels. With such constraints, certain problems have arisen. Water-dispersed systems are slow to dry. Not only do they result in wetness on the hair but there is also an undesirable initial curl droopage due to water being placed on the curl. Quite significantly there is also difficulty in developing the style. Resins formulated in a water-based system can have weak holding power.

A body of literature has developed that attempts to meet these environmental related challenges. Replacement of chlorofluorocarbons with hydrocarbon propellants has been discussed in U.S. Pat. No. 4,859,455 (Nowak, Jr. et al.). Improved tolerance to the hydrocarbon levels was reported as being achieved through neutralization of acrylic resins with mixtures of sodium or potassium hydroxide and certain long chain amines. U.S. Pat. No. 5,021,238 (Martino et al.) reports the further advance of using dimethyl ether (DME) as a hairspray propellant. DME allows use of water as the only solvent thereby significantly reducing the volatiles problem.

Recently there has been disclosed in U.S. Pat. No. 5,068,099 (Sramek) an aerosol hairspray package claiming reduced volatile organic compound emission during the useful life of the package. The spray composition contains a combination of at least two polymers differing in weight average molecular weight by at least 1.5. This blend of polymers combines with a low delivery rate discharge mechanism to provide an atomized composition with mean particle size of at least 60 microns. A significant drawback of this technology is the necessity for very substantial amounts of volatile alcohol; water is present at levels no higher than 10% by weight. Instead of eliminating volatiles from the formula, the patent merely controls the spray emission thereof. Unfortunately, at some point in the life cycle of the package, volatiles will be emitted into the atmosphere.

Even though there have been significant advances in this art, many problems still remain. Some systems are excellent at reducing volatile organic compounds but hair hold, wetness and other physical properties are not equivalent to the old volatile solvent-based formulas. In other instances, physical properties are excellent but there is either insufficient volatiles reduction or the systems are too costly.

Accordingly, it is an object of the present invention to provide a hairspray composition that reduces volatile organic compound emissions to the atmosphere thereby being environmentally friendly.

Another object of the present invention is to provide a hairspray composition which is a water-based system.

A further object of the present invention is to provide a hairspray composition for a water-based system that has improved holding and styling characteristics.

A still further object of the present invention is to provide a hairspray composition for a water-based system that dries fairly quickly and does not impart any undue wet or cool feel to hair or scalp.

These and other objects of the present invention will become more evident from the following summary and detailed description.

SUMMARY OF THE INVENTION

An aqueous hairspray composition is provided including:

(i) a nonionic film-forming polymer constituted from at least one monomer having at least one unneutralized carboxylic acid group; and (ii) an anionic film-forming polymer which is the nonionic film-forming polymer all of whose carboxylic acid groups have been converted to a salt form;

the relative weight ratio of nonionic to artionic film-forming polymer ranging from about 10:1 to about 1:10.

Compositions of this invention can further include an acrylic resin constituted from at least one monomer having at least one carboxylic group, all of the carboxylic groups being in salt form. Advantageously, the acrylic resin is a water-soluble amphoteric polymer with carboxylic groups neutralized with an appropriate neutralizing agent. This resin is preferably randomly neutralized with a water soluble $C_8$–$C_{22}$ fatty amine and an alkali metal base, ammonia, a $C_1$–$C_6$ alkanolamine or a $C_1$–$C_6$ alkyl amine.

In a further aspect of the invention, the composition includes a $C_2$–$C_4$ alkylene carbonate to plasticize the polymers and to help better wet surfaces of the hair.

Hairspray compositions of this invention are dispersed in water which may contain from 0–50% of a propellant such as dimethyl ether.

DETAILED DESCRIPTION

It has been discovered that many of the objects of the present invention can be achieved through a composition that includes a nonionic water insoluble film-forming polymer having at least one monomer with at least one unneutralized carboxylic acid group in conjunction with an anionic film-forming polymer, of identical structure to the nonionic polymer except that all the carboxylic acid groups are neutralized with a neutralizing agent into a salt form. In water, the anionic polymer will be present as a solubilized resin while the nonionic polymer will be present as an insoluble resin dispersion. Three functions are served by the artionic polymer. Firstly, the artionic plasticizes the nonionic polymer. Secondly, the anionic polymer coats hair to improve wettability. Thirdly, the whole system is stabilized by the anionic polymer so that the product does not cream.

The nonionic insoluble polymer dispersion serves several functions. Firstly, it releases water from the drying film faster than the artionic solution, allowing faster drying. Secondly, it increases the overall solids content without building viscosity or destroying the sprayability of the overall system. By contrast, soluble high molecular weight anionics in sufficient quantitities will not allow proper atomization of the system even though the solution viscosity may be low. This limits the concentration of the anionic polymer species as high concentrations will decrease sprayability.

The nonionic film-forming polymer must be constituted of at least one polymer having at least one unneutralized carboxylic acid group as part of its structure. Typical monomers include those selected from the group consisting of acrylic acid, methacrylic acid, crotonic acid, fumaric acid, maleic acid, itaconic acid and combinations thereof. Amounts of the monomer with the at least one carboxylic acid group will be present from about 1 to about 80%, preferably from about 3 to about 50%, optimally from about 5 to about 30% by weight of the total nonionic polymer. Comonomers forming the nonionic polymer may be selected from the group consisting of α-methylstyrene, styrene, divinylbenzene, vinyl acetate, vinyl neodecanoate, acrylamide, methacrylamide, $C_1$–$C_{20}$ esters of acrylic or methacrylic acids, $C_1$–$C_{20}$ esters of maleic or fumaric acids and combinations thereof. Amounts of the hydrophobic comonomers will range from about 20 to 99%, preferably from about 50 to 97%, optimally from about 70 to about 85% by weight. Preferred nonionic polymers include: methacrylic acid/methyl methacrylate/ethyl acrylate; methacrylic acid/styrene/butytacrylate; methacrylic acid/methyl methacrylate/butyl acrylate; acrylic acid/vinylacetate/butyl acrylate. Most preferred is 5–15% methacrylic acid/30–40% methyl methacrylate/50–60% ethyl acrylate, available from the Amerchol Company.

Amounts of the nonionic polymer will range from about 0.5 to about 10%, preferably from about 1 to about 8%, optimally from about 2 to about 6% by weight.

A second essential element of compositions according to the present invention is an artionic film-forming polymer. The anionic polymer will be identical to the nonionic polymer, except that all of the carboxylic acid groups will be neutralized into salt form. Typical cations forming the salt as counterions to the carboxylate groups are those selected from the group consisting of alkalimetal, alkaline earth metal, ammonium, $C_1$–$C_6$ alkanotammonium, $C_1$–$C_{22}$ alkyl ammonium cations and combinations thereof. Examples of suitable neutralizing agents that form the aforementioned cations include sodium hydroxide, potassium hydroxide, 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); and triisopropanolamine (TRIPA).

Amounts of the artionic polymer will range from about 0.5 to about 10%, preferably from about 1 to about 8%, optimally from about 1.5 to about 4% by weight.

Best performance of compositions according to the present invention is achieved with the additional presence of an acrylic film-forming resin constituted from at least one monomer with at least one carboxylic group, all of the at least one carboxylic groups being in salt form. Preferably the acrylic resin is amphoteric. Illustrative of monomers with the at least one carboxylic group are acrylic acid and salts thereof, methacrylic acid and salts thereof, maleic acid and salts thereof, fumaric acid and salts thereof, crotonic acid and salts thereof and mixtures of these monomers. Amounts of the aforementioned monomers may range from about 1 to about 99% by weight. Illustrative comonomers that will contribute positive charge to form the amphoteric structure are $C_1$–$C_8$ alkyl aminomethacrylate, $C_1$–$C_8$ alkylaminoacrylate and mixtures thereof. Typical comonomers are t-butylaminoethyl methacrylate, t-butylaminopropyl acrylate, N,N-diethylaminoethyl acrylate, N,N-dimethylaminoethyl methacrylate and combinations thereof. Amounts of the comonomer will range from about 1 to about 30%, preferably from about 5 to about 20% by weight of the acrylate polymer. Most preferred is a resin copolymer of octyl acrylamide/acrylates/butylaminoethyl methacrylate, available under the trademark Amphomer® from the National Starch and Chemical Corporation, Bridgewater, N.J.

A particularly preferred embodiment of the acrylic resin is where the carboxylic groups are randomly neutralized to a salt form having a cation selected from the group consisting of ammonium, alkalimetal (such as potassium or sodium), $C_1$–$C_6$ alkanolammonium and $C_1$–$C_6$ alkylammonium cations. In conjunction therewith the resin is also randomly neutralized with a water soluble $C_8$–$C_{22}$ fatty ammonium cation derived from a respective amine neutralizing agent. Relative weight amounts of the first and second acrylic neutralizing agents will range from about 10:1 to 1:10, preferably from about 5:1 to 1:5, optimally between about 2:1 and 1:2. Most preferred is a combination of Amphomer® resin neutralized with potassium hydroxide in combination with a second neutralizing agent of a water soluble PEG-5 cocoamine such as Ethomeen C15®.

The acrylic resin functions to plasticize both the nonionic and anionic polymers but will stop short of solubilizing them, solubilization preventing the sprayability of the polymers. This resin also functions to improve washability of the overall system. Optimum plasticization is achieved by the combination of different neutralization counterions and the ratios of the long chain amine to short chain amine or inorganic alkali base neutralizing agent.

Amounts of the acrylic resin within compositions of this invention may range from about 0.5 to about 10%, preferably from about 1 to about 5%, optimally between about 1.5% and 3% by weight.

Relative weight ratios of nonionic to anionic polymer will range from about 10:1 to about 1:10, preferably from about 5:1 to about 1:5, optimally from about 3:1 to 1:2. The relative weight ratio of nonionic and artionic polymer combined to that of the acrylic resin, when present, will range from about 30:1 to about 1:2, preferably from about 15:1 to about 5:1, optimally about 10:1.

Compositions of the present invention will also include water as a carrier for the polymers and other components. Water will be present in amounts ranging from about 20% to about 99%, preferably from about 40% to about 95% by weight. Optimally, water will be the major if not exclusive liquid carrier for the hair treatment compositions of this invention. Volatile organic solvents such as methanol, ethanol or isopropanol are preferably absent, but may be present to aid drying or reduction of vapor pressure of the propellant.

The present hair treatment compositions may be formulated as sprays in aerosol or nonaerosol forms. If an aerosol hairspray is desired, a propellant must be included in the composition. This agent is responsible for expelling the other materials from the container and forming the hairspray character.

The propellant gas will be a $C_1$–$C_6$ alkyl ether, most preferably dimethyl ether. Amounts of the ether will range from about 10 to about 45%, preferably from about 30 to about 40%, optimally between about 32 and 37% by weight.

Small quantities of surfactant ranging anywhere from about 0.1 to about 10%, preferably from about 0.1 to about 1%, optimally about 0.3% by weight, may be present in the compositions of the invention. The surfactant may be an anionic, nonionic or cationic emulsifier. Particularly preferred are nonionic emulsifiers which are formed from alkoxylation of hydrophobes such as fatty alcohols, fatty acids and phenols. Illustrative of such material is Triton X-100, and isoctyl phenyl polyethoxyethanol. Fluorinated surfactants such as Zonyl® available from DuPont are particularly preferred and can be used in conjunction with the other surfactants.

Another useful component of compositions according to the present invention is that of a $C_2$–$C_4$ alkylene carbonate present in an amount from about 0.05 to 1.0%, preferably from about 0.1 to 0.8%, optimally between about 0.2 and 0.5% by weight. Most preferred is propylene carbonate. This material functions as a co-plasticizer and also helps to better wet the surface of hair.

Another useful plasticizer is Lubrigel® available from the Dash Company. This material is a combination of glycerin and methacrylic acid. Amounts may range from about 0.1 to 2% by weight.

Compositions of this invention may contain any other ingredient normally used in hairsprays. These other ingredients may include antifoam agents, proteins, antioxidants, fragrances, antimicrobials and sunscreens. Each of these ingredients will be present in an amount effective to accomplish its purpose.

Hairspray formulations of the present invention may, if desired, be packaged in a pump spray container operated without any propellant. Otherwise, the composition may be charged into a suitable pressurizable container which is sealed and then charged with propellant according to conventional techniques.

The following examples will more fully illustrate the embodiments of this invention. All parts, percentages and proportions referred to herein and in the appended claims are by weight unless otherwise indicated.

EXAMPLE 1

A pair of hairspray compositions corresponding to the present invention are displayed in Tables I and II. Performance tests of these hairsprays against a typical commercial alcohol/hydrocarbon propellant product indicated at least as good hold and wetness control properties. The results were surprising in view of the considerable water present in the test formula.

TABLE I

| COMPONENT | WEIGHT % |
|---|---|
| Phase A | |
| Amphomer LV 71 ® | 2.380 |
| Potassium Hydroxide (87%) | 0.292 |

TABLE I-continued

| COMPONENT | WEIGHT % |
|---|---|
| Deionized Water | 26.279 |
| Ethomeen C15 ® | 0.474 |
| Phase B | |
| Methacrylic Acid/Methyl methacrylate/ Ethyl acrylate (25% dispersion) | 18.960 |
| Lubrigel ® | 0.790 |
| Propylene Carbonate | 0.395 |
| Zonyl FSP ® | 0.200 |
| Fragrance | 0.105 |
| Triton X-100 ® | 0.100 |
| Antifoam | 0.025 |
| Phase C | |
| Methacrylic Acid/Methyl methacrylate/ Ethylacrylate (15% solution potassium hydroxide neutralized) Propellant | 13.000 |
| Dimethyl Ether | 37.000 |

TABLE II

| COMPONENT | WEIGHT % |
|---|---|
| Phase A | |
| Deionized Water | 37.490 |
| Potassium Hydroxide (87%) | 0.300 |
| Methacrylic Acid/Methyl methacrylate/Ethyl acrylate (25% dispersion) | 6.240 |
| Phase B | |
| Amphomer 4910 ® | 1.900 |
| Ethomeen C15 ® | 0.310 |
| Phase C | |
| Lubrigel ® | 0.630 |
| Propylene Carbonate | 0.630 |
| Zonyl FSP ® | 0.100 |
| Triton X-100 ® | 0.100 |
| Antifoam | 0.025 |
| Phase D | |
| Methacrylic Acid/Methyl methacrylate/Ethylacrylate (20% dispersion) | 15.170 |
| Phase E | |
| Dimethyl Ether | 37.000 |

EXAMPLE 2

A series of hairspray compositions were formulated to evaluate the effect of relative weight ratio of nonionic to anionic film-forming polymer. Compositions of these hairsprays and their performance are listed under Table III.

TABLE III

| | SAMPLE (WT. %) | | | |
|---|---|---|---|---|
| | A | B | C | D |
| Phase A | | | | |
| Amphomer LV 71 ® | 2.380 | 2.380 | 2.380 | 2.380 |
| Potassium Hydroxide (87%) | 0.292 | 0.292 | 0.292 | 0.292 |
| Deionized Water | 29.809 | 26.279 | 22.546 | 15.119 |
| Ethomeen C15 ® | 0.474 | 0.474 | 0.474 | 0.474 |
| Phase B | | | | |
| Triton X-100 ® | 0.100 | 0.100 | 0.100 | 0.100 |
| Lubrigel ® | 0.790 | 0.790 | 0.790 | 0.790 |
| Propylene Carbonate | 0.355 | 0.355 | 0.355 | 0.355 |
| Fragrance | 0.105 | 0.105 | 0.105 | 0.105 |
| Dow Corning ® Antifoam | 0.025 | 0.025 | 0.025 | 0.025 |
| Phase C | | | | |
| Methacrylic Acid/Methylmethacrylate/Ethyl Acrylate (25% dispersion) | 24.400 | 18.860 | 13.400 | 2.400 |
| Phase D | | | | |
| Methacrylic Acid/Methylacrylate/Ethyl Acrylate (15% solution potassium hydroxide neutralized to pH 9.05) | 4.070 | 13.000 | 22.333 | 40.660 |
| Phase E | | | | |
| Dimethyl Ether | 37.000 | 37.000 | 37.000 | 37.000 |
| Ratio of Nonionic to Anionic Polymer | 10:1 | 2.4:1 | 1:1 | 1:10 |
| Physical Properties | | | | |
| Viscosity (cps) | 9 | 19.5 | 24 | 30 |
| pH | 7.07 | 7.26 | 7.8 | 8.44 |
| Performance | | | | |
| Sprayability | excellent | excellent | excellent | poor |
| Rinsability | poor | excellent | excellent | excellent |
| Appearance (when sprayed on hair) | white droplets of poor wettability | semi-clear droplets of good wettability | semi-clear droplets of good wettability | clear droplets of good wettability Foams-Very large droplets |
| Hair Hold | poor | excellent (stiff) | excellent (stiff) | unacceptable (due to poor spray) |
| Film Properties | somewhat brittle | excellent (flexible) | excellent (flexible) | excellent (flexible) |

When the ratio of nonionic to artionic polymer is 10:1, as in Sample A, the hairspray has excellent sprayability but is borderline rinseable and the film is somewhat brittle. On the reverse ratio Sample D, sprayability is only borderline but rinseability and film properties are excellent. Optimum performance is seen for Samples B and C with respective ratios of 2.4:1 and 1:1. Sprayability, rinseability and film properties of B and C are all excellent.

EXAMPLE 3

Another series of hairspray compositions were prepared to evaluate various criticalities of the present invention.

The formula of Sample E is listed below.

| SAMPLE E | |
|---|---|
| COMPONENTS | WEIGHT % |
| Methacrylic Acid/Methyl Methacrylate/Ethyl Acrylate (25% dispersion) | 37.000 |
| Deionized Water | 25.000 |
| Fragrance | 0.1200 |
| Dimethyl Ether | 37.000 |

The pH of this hairspray was 6.90 and viscosity was 3.5 cps. This hairspray was placed in an aerosol can and sprayed onto hair swatches. Sprayability was excellent with the spray easily being broken up into fine particles. However, when sprayed onto the hair swatch, the presence of white droplets were observed which did not wet out well onto the hair shafts. A subjective evaluation determined that there was poor hold and stiffness when compared to a standard commercial spray such as Rave® No. 3. Rinseability was poor with large white flakes left on the hair. Film properties were also poor, being brittle and powdery with no flexibility. The conclusion drawn from this experiment is that a nonionic polymer in dispersion form, in the absence of any anionic polymer, is unsuitable as a hairspray.

The formula of Sample F is listed below.

SAMPLE F

| COMPONENTS | WEIGHT % |
| --- | --- |
| Methacrylic Acid/Methylmethacrylate/Ethyl Acrylate (25% dispersion) | 60.000 |
| Potassium Hydroxide (50% solution) | 1.700 |
| Deionized Water | 38.000 |

The above composition was neutralized to pH 9.47 and formed a clear solution of polymer with minimal Tyndall effect. Viscosity of the solution was 17 cps. This composition was then formulated into a pair of aerosol hairspray products with the finished products being the formulas listed below.

TABLE IV

| | FORMULA F (Weight %) | FORMULA F' (Weight %) |
| --- | --- | --- |
| Methacrylic Acid/Methylmethacrylate/Ethyl Acrylate | 37.80 | 32.00 |
| Potassium Hydroxide (50% Solution) | 1.07 | 0.905 |
| Deionized Water | 24.13 | 30.095 |
| Dimethyl Ether | 37.00 | 37.00 |
| % Solids | 9.45 | 8.00 |

Sample F was unsprayable. It streamed and foamed upon exit from the spray nozzle. Sample F' was better but still not acceptable.

These samples were sprayed onto hair swatches despite the very poor spray quality, the materials wetted well the hair shafts with clear liquid. Subjective evaluation indicated excellent hold that appeared equivalent to Rave® No. 3. Film properties were good. A continuous film formed of good flexibility. Rinseability was also very good. The resins washed out of the hair swatches very well leaving no residuals.

Based on the foregoing results, we conclude that a totally neutralized polymer system such as the anionic film-forming polymer alone would not be suitable for use as a hairspray at higher resin levels due to poor sprayability. However, neutralization did improve rinseability, film properties, hold and wetting out of solution onto the hair shaft.

In the following experiment the resins utilized for samples E and F were combined, into one system. The formulation is listed below.

SAMPLE G

| COMPONENTS | WEIGHT % |
| --- | --- |
| Methacrylic Acid/Methylmethacrylate/Ethyl Acrylate (25% Dispersion) | 20.000 |
| Methacrylic Acid/Methylmethacrylate/Ethyl Acrylate (15% Solids Neutralized with Potassium Hydroxide to pH 9.45) | 33.000 |
| Deionized Water | 17.000 |
| Dimethyl Ether | 37.000 |

Total resin solids was 10%. The pH of the hairspray was 7.08 with viscosity of 14 cps.

Excellent sprayability was achieved with the desired fine breakup of particles. Upon wetting out onto the hair shafts, there was little evidence of white droplets as seen with the unneutralized dispersion.

Sample G was comparable to Rave® No. 3 in stiffness. However, bonds broke easily with flexing and rinseability was not quite acceptable. There were some definite deposits left on the hair in the form of flakes. Film properties were more brittle than the neutralized sample and performance was not comparable to Rave® No. 3 (control).

From this we conclude the combination of the dispersion (nonionic) and neutralized (anionic) polymers can provide a high solids sprayable system. However, film properties, rinseability and hold would not be quite sufficient for commercial purposes.

In the following experiment, Sample G was repeated in a single step process to eliminate use of two separate blending tanks. The formula of Sample H is listed below.

SAMPLE H

| COMPONENTS | WEIGHT % |
| --- | --- |
| Methacrylic Acid/Methylmethacrylate/Ethyl Acrylate (25% Dispersion) | 40.000 |
| Potassium Hydroxide (87% Pellets) | 0.587 |
| Deionized Water | 22.413 |
| Dimethyl Ether | 37.000 |

The procedure here involved dissolving potassium hydroxide into water to which was added the polymer dispersion while mixing until homogeneous. The resulting concentrate had a pH of 7.95 with viscosity of 310 cps.

The formula was filled into an aerosol can. The resulting product was not sprayable, demonstrating streaming and foaming upon ejection from the aerosol can.

In the following example, Sample I, the single step process was again utilized but the polymer was added in such a manner that only half of the dispersion was completely neutralized and the other half completely unneutralized (as in Sample G).

SAMPLE I

| COMPONENTS | WEIGHT % |
| --- | --- |
| Methacrylic Acid/Methylmethacrylate/Ethyl Acrylate (25% Dispersion) | 40.000 |
| Potassium Hydroxide (87% Pellets) | 0.587 |
| Deionized Water | 22.413 |
| Dimethyl Ether | 37.000 |

Formation of the concentrate was achieved by dissolving potassium hydroxide in water and then adding half of the polymer dispersion while mixing. Upon obtaining a uniform solution, the remaining half of the polymer dispersion was added. By this procedure, all of the first half of the polymer dispersion had its carboxylate groups neutralized while none of the second half polymer dispersion was neutralized. This procedure avoided a random neutralization of the total polymer dispersion.

At the completion of the addition of the first half of the polymer dispersion, the concentrate was a clear solution which then reverted back into a milky dispersion upon addition of the second half of the polymer. The pH of the resulting sample was 7.90 with viscosity of 28 cps.

The sample was filled into an aerosol. Good sprayability and break-up of particles was observed.

Results from this sample demonstrated that for optimum performance it is necessary to have the polymer dispersion in two distinct forms. One form must be completely neutralized and the other form completely unneutralized. Random neutralization of all the polymer dispersion as in Example H results in a non-sprayable concentrate.

The foregoing description and Examples illustrate selected embodiments of the present invention. In light thereof, various modifications will be suggested to one skilled in the art, all of which are within the spirit and purview of this invention.

What is claimed is:

1. An aqueous hairspray composition comprising:
   (i) a nonionic film-forming polymer constituted from at least one monomer having at least one unneutralized carboxylic acid group; and
   (ii) an anionic film-forming polymer which is identical to the nonionic film-forming polymer except that all of the carboxylic acid groups have been converted to a salt form; the relative weight ratio of nonionic to anionic film-forming polymer ranging from about 10:1 to about 1:10.

2. A composition according to claim 1 further comprising from about 0.5 to about 10% of an amphoteric acrylic film forming resin constituted from at least one monomer having at least one carboxylic group, all of the carboxylic groups being in salt form.

3. A composition according to claim 2 wherein the amphoteric resin is a copolymer of octyl acrylamide/acrylates/butylaminoethyl methacrylate.

4. A composition according to claim 2 wherein the total weight ratio of nonionic and anionic polymers combined to acrylic resin ranges from about 30:1 to about 1:2.

5. A composition according to claim 4 wherein the total weight ratio ranges from about 15:1 to about 5:1.

6. A composition according to claim 1 wherein the salt form of the anionic polymer comprises a cation selected from the group consisting of ammonium, alkalimetal, alkaline earth metal, $C_1$–$C_{22}$ alkyl ammonium, $C_1$–$C_6$ alkanolammonium and cation combinations thereof.

7. A composition according to claim 3 wherein the acrylic resin is randomly neutralized to a pair of salt forms, a first of the salt forms having a cation selected from the group consisting of ammonium, alkalimetal, alkaline earth metal, $C_1$–$C_6$ alkylammonium and $C_1$–$C_6$ alkanolammonium cations, and a second of the salt forms having a cation which is a water soluble $C_8$–$C_{22}$ fatty ammonium cation, the relative weight ratio of first to second salt forms ranging from about 5:1 to about 1:5.

8. A composition according to claim 1 wherein the nonionic polymer is formed from monomers with at least one unneutralized carboxylic acid selected from the group consisting of acrylic acid, methacrylic acid, fumaric acid, maleic acid, crotonic acid, itaconic acid and combinations thereof.

9. A composition according to claim 8 wherein the nonionic polymer is a copolymer of methacrylic acid/methyl methacrylate/ethyl acrylate.

10. A composition according to claim 1 further comprising from about 10 to about 45% dimethyl ether as a propellant.

11. A composition according to claim 10 wherein the dimethyl ether is present in an amount from about 30 to about 37% and is the sole propellant.

12. A method for treating hair to impart improved holding and styling characteristics comprising spraying onto the hair an aqueous hairspray composition comprising:
   (i) a nonionic film-forming polymer constituted from at least one monomer having at least one unneutralized carboxylic acid group; and
   (ii) an anionic film-forming polymer which is identical to the nonionic film-forming polymer except that all of the carboxylic acid groups have been converted to a salt form;
   the relative weight ratio of nonionic to anionic film-forming polymer ranging from about 10:1 to about 1:10.

13. The method according to claim 12 wherein the composition further comprises from about 0.5 to about 10% of an amphoteric acrylic film forming resin constituted from at least one monomer having at least one carboxylic group, all of the carboxylic groups being in salt form.

* * * * *